US009684005B2

(12) United States Patent
Gussakovsky et al.

(10) Patent No.: US 9,684,005 B2
(45) Date of Patent: Jun. 20, 2017

(54) APPARATUS AND METHOD FOR SPECTROSCOPIC ANALYSIS OF VINIFICATION LIQUIDS USING CODED SAMPLE CONTAINERS

(71) Applicant: BL Photonics Inc., Winnipeg (CA)

(72) Inventors: Eugene Gussakovsky, Winnipeg (CA); Efim Gussakovsky, Winnipeg (CA)

(73) Assignee: BL PHOTONICS INC., Winnipeg, Manitoba (CA)

( * ) Notice: Subject to any disclaimer, the term of this patent is extended or adjusted under 35 U.S.C. 154(b) by 79 days.

(21) Appl. No.: 14/556,968

(22) Filed: Dec. 1, 2014

(65) Prior Publication Data

US 2015/0160248 A1 Jun. 11, 2015

Related U.S. Application Data

(60) Provisional application No. 61/912,682, filed on Dec. 6, 2013.

(51) Int. Cl.
| | |
|---|---|
| *G01J 3/28* | (2006.01) |
| *G01N 35/00* | (2006.01) |
| *G01N 21/25* | (2006.01) |
| *G01N 33/14* | (2006.01) |

(52) U.S. Cl.
CPC ..... *G01N 35/00732* (2013.01); *G01N 21/255* (2013.01); *G01N 33/146* (2013.01); *G01N 35/00871* (2013.01); *G01N 2035/00752* (2013.01); *G01N 2035/00821* (2013.01); *G01N 2035/00881* (2013.01); *G01N 2201/0256* (2013.01)

(58) Field of Classification Search
CPC ... G01N 35/00732; G01N 2035/00752; G01N 2035/00801; G01N 2035/00861; G01N 33/146; G06K 1/121; B01L 3/5453
See application file for complete search history.

(56) References Cited

U.S. PATENT DOCUMENTS

| | | | | |
|---|---|---|---|---|
| 5,397,709 | A * | 3/1995 | Berndt | G01N 21/253 356/442 |
| 7,218,395 | B2 * | 5/2007 | Kaye | B07C 5/344 356/301 |

(Continued)

*Primary Examiner* — Kara E Geisel
*Assistant Examiner* — Maurice Smith
(74) *Attorney, Agent, or Firm* — Kyle R. Satterthwaite; Ryan W. Dupuis; Ade & Company Inc.

(57) ABSTRACT

An apparatus for spectroscopic analysis of vinificition liquids features a sample holder for a sample container of vinification liquid, a light source for directing a beam of light into the sample supported by the sample holder, a spectrometer arranged for receiving and measuring the beam of light after interaction thereof with the sample in order to perform a spectroscopic scan of the sample and generate measured spectral data thereon, and a scanning device positioned for scanning a machine readable code on the sample container. A computing device in communication with the spectrometer and the scanning device applies a classification to the measured spectral data of the sample according to a classification code read from the sample container. The classification code is used to determine what parameters should be calculated from the spectral data for the particular sample in question.

23 Claims, 4 Drawing Sheets

(56) References Cited

U.S. PATENT DOCUMENTS

| | | | |
|---|---|---|---|
| 8,699,020 B1* | 4/2014 | Zhou | G01J 3/0264 356/301 |
| 2003/0129654 A1* | 7/2003 | Ravkin | G01N 33/54313 435/7.1 |
| 2003/0136837 A1* | 7/2003 | Amon | G07D 7/06 235/435 |
| 2004/0018485 A1* | 1/2004 | Ravkin | B01J 19/0046 435/4 |
| 2006/0058724 A1* | 3/2006 | Handfield | A61J 7/0084 604/20 |
| 2006/0228802 A1* | 10/2006 | Tiller | G01N 27/333 436/56 |
| 2008/0182301 A1* | 7/2008 | Handique | B01L 3/502715 435/91.2 |
| 2009/0214088 A1* | 8/2009 | Sorenson | G01N 1/312 382/128 |
| 2011/0148606 A1* | 6/2011 | Glee | G06Q 10/1091 340/309.7 |
| 2012/0228381 A1* | 9/2012 | Drzymala | G06K 7/10554 235/440 |
| 2014/0085630 A1* | 3/2014 | Bell | G01J 3/28 356/301 |

\* cited by examiner

APPARATUS AND METHOD FOR SPECTROSCOPIC ANALYSIS OF VINIFICATION LIQUIDS USING CODED SAMPLE CONTAINERS

CROSS REFERENCE TO RELATED APPLICATIONS

This application claims benefit under 35 U.S.C. 119(e) of Provisional Application Ser. No. 61/912,682, filed Dec. 6, 2013, the entirety of which is incorporated herein by reference.

FIELD OF THE INVENTION

The present invention relates generally to spectroscopic analysis of wine, and/or liquids used in the preparation of wine, which are collectively referred to herein as vinification liquids.

BACKGROUND OF THE INVENTION

In the field of winemaking, it is known to use spectroscopic analysis of wines and substances used in the preparation of wines (e.g. grape musts), in order to perform quantitative and qualitative determination of components of such liquids.

For example, an optical spectrometry based assay system for vinification liquids is disclosed in U.S. Pat. No. 6,885,003.

Another device for spectroscopic assay of a liquid vinification product is disclosed in U.S. Patent Application Publication No. 2010/0091279.

Wine is a complex substance, in which there are a vast variety of components that have a significant effect on the quality and character of the wine. Accordingly, a thorough analysis of a wine can require measurement of a notable number of parameters. Different types of parameters include content (concentration) of compounds, and physical and physico-chemical properties of the specimen. Examples of some parameters include alcohol content, sugar content, acidity, color, phenols and anthocyanins contents, other wine constituents which are critical for wine quality.

Commercially available spectroscopic solutions for wine analysis include multiparameter systems capable of measuring several parameters (e.g. FOSS Winescan™), but carry a notable expense that may not be justifiable as an in-house analysis option for a smaller winery. Photometer-based single parameter wine analyzing devices are available on a more affordable basis (e.g. wine photometers by HANNA Instruments), but mean that only one parameter can be measured, or that a collection of multiple devices is required to measure more than one parameter.

A known alternative to in-house wine assaying equipment is the use of an independent outside laboratory to perform the analysis, but has the added complication of requiring transport of the wine samples to the laboratory, may be more costly and significantly time consuming since the full testing process (preparation of suitable test samples, calibration of equipment, measurement procedures, and processing of the results) is carried out entirely by the staff of the outside laboratory.

Determination of a significant number of wine parameters requires preparation of an extensive number of test samples, as the determination of many of the parameters of interest requires either mixing the wine with a particular reagent prior to the spectroscopic scan, or performing scans of different samples in which the wine has been mixed with different reagents or reagent mixtures. Accordingly, multi-parameter assaying of wine conventionally requires a technician with in-depth specialized knowledge to ensure that the samples are prepared and analyzed correctly, and the data results from the scans are handled and processed appropriately to gain accurate and meaningful results.

Some effort in the area of photometric analysis has previously been made to partially automate the test process to reduce the number of steps required by the technician to reduce the potential for error. Particularly, U.S. Pat. No. 5,386,287 and U.S. Patent Application Publication 2013/0217141 disclose the idea of employing a barcode scanner in combination with a photometer and equipping sample cuvettes with barcode labels that are read by the scanner in order to retrieve calibration data used to calibrate the photometer according to a pre-filled reagent contained within the cuvette. This avoids erroneous results that may come from an inadvertent mismatch between technician-controlled calibration conditions of the photometer and the particular analyte/reagent combination being scanned in the cuvette.

However, the barcode data in these prior art solutions is not used for any tracking, management or processing of the output data from the photometer. Accordingly, in the case of spectroscopic wine analysis, where multi-parameter testing capabilities requires processing of the spectral data from a significant number of different scans, the prior art concept of using the barcode to calibrate the measurement equipment does nothing to prevent erroneous application of the measured data in the subsequent processing from which useful information is derived from the raw measurement data. Accordingly, skilled expertise would still be required Accordingly, there remains a need in the art for an affordable multi-parameter spectroscopic wine analysis system and process by which non-specialized winery personnel can perform spectroscopic scans of vinification liquids and obtain accurate error-free and meaningful results without in-depth training or knowledge on the complexities of such spectroscopic analysis.

SUMMARY OF THE INVENTION

According to one aspect of the invention there is provided an apparatus for spectroscopic analysis of vinificition liquids, the apparatus comprising:

a sample holder arranged to support a sample container containing a sample of a vinification liquid;

a light source arranged relative to the sample holder to direct a beam of light into the sample in the sample container when the sample container is supported by the sample holder;

a spectrometer arranged relative to the sample holder to receive and measure the beam of light after interaction thereof with the sample in order to perform a spectroscopic scan of the sample and generate measured spectral data thereon;

a scanning device positioned relative to the sample holder to scan a machine readable code on the sample container when the sample container is supported by the sample holder; and a computing device in communication with the spectrometer and the scanning device, the computing device being configured apply a classification to the measured spectral data of the sample according to a classification code read from the sample container.

The light source, the spectrometer and the scanning device may all be contained within a common housing.

Preferably the housing comprises an openable and closable access cover movable between a closed position concealing the sample holder and an open position revealing access to the sample holder.

Preferably the computing device is a mobile general computing device and the housing comprises a docking port having a communication connector to which the mobile general computing device is detachably connected to establish a communication link of the mobile general computing device with both the spectrometer and the scanning device.

Preferably the docking port supports the mobile general computing device on the housing in a working position in which a display screen of the general computing device is visible at an exterior of the housing.

Preferably the docking port is positioned proximate a rear end of the housing and configured to face the display screen forwardly over a topside of the housing toward an opposing front end of the housing, the sample holder being accessible from the topside of the housing at a location between the docking port and the front end of the housing.

Preferably the mobile general computing device comprises a processor, a touchscreen display defining the display screen, and computer readable memory having stored thereon statements and instructions for execution by the processor to display a touchscreen graphical user interface of an application for controlling the spectrometer and managing the measured spectra data from said spectrometer.

Preferably the computing device comprises a processor, a display, and computer readable memory having stored thereon statements and instructions for execution by the processor to (a) display a graphical user interface of a software application and (b) via said graphical user interface, perform the steps of (i) prompting a user to enter batch identification information for a batch of vinificition liquid from which samples are to be analyzed; (ii) in response to confirmation of receipt of a respective sample container containing a respective sample of the vinification liquid at the sample holder, reading the machine readable code from the respective sample container; (iii) subject to successful reading of the machine readable code, triggering the light source and the spectrometer to perform said spectroscopic scan; and (iv) receiving the measured spectral data from said spectroscopic scan and storing said spectral data in association with both the batch identification information and the classification applied to said spectral data.

The statements and instructions for execution by the processor may be further configured to transmit the measured spectral data to a remote server via a communications network for further processing of the spectral data to determine a quantitative measurement for one or more parameters of the batch of vinification fluid.

There may be provided a data hub electronically connected to the spectrometer and the scanning device to at least partly define a single communication link by which the spectrometer and the scanning device communicate with the computing device.

Preferably the sample holder and the scanning device are arranged to remain stationary relative to one another during scanning of the machine readable code.

According to a second aspect of the invention there is provided a method for spectroscopic analysis of vinificition liquids, the method comprising the steps of:
(a) scanning a machine-readable code on a sample container that contains a sample comprising a vinification liquid;
(b) performing a spectroscopic scan of the sample to obtain a measured spectral data set on said sample;
(c) automatically applying a classification to the measured spectral data set of the sample according to a classification code read from the machine-readable code of the sample container.

The method may include step (d) of repeating steps (a) through (c) for multiple sample containers comprising respective samples from a common batch of the vinification liquid, and step (e) of transmitting the measured spectral data set and applied classification for each sample to a remote server at which values for different characterizing parameters of the vinification liquid are calculated by (ii) selecting, for each characterizing parameter, one or more of the measured spectral data sets for which the applied classification matches a prescribed set of one or more required classification types needed to calculate the characterizing parameter; and (ii) using the selected one or more spectral data sets to calculate to the characterizing parameter.

Alternatively step (d) may comprise repeating steps (a) through (c) for multiple sample containers comprising respective samples from a common batch of the vinification liquid, and step (e) of calculating values for different characterizing parameters of the vinification liquid by (ii) selecting, for each characterizing parameter, one or more of the measured spectral data sets for which the applied classification matches a prescribed set of one or more required classification types needed to calculate the characterizing parameter; and (ii) using the selected one or more spectral data sets to calculate to the characterizing parameter.

According to a third aspect of the invention there is provided a server for communication with a remote terminal configured to generate and transmit measured spectral data for samples comprising vinification liquids, the server comprising a processor and computer readable memory having stored thereon statements and instructions for execution by the processor to perform the steps of:
(a) over a communications network, receiving respective measured spectral data sets for of a plurality of samples for which the vinification liquid was sourced from a common batch of said vinification liquid, along with classifications applied to said measured spectral data sets by the remote terminal;
(b) for each of a plurality of characterizing parameters to be determined for said common batch of said vinification liquid, (i) looking up a prescribed set of one or more classification types required to determine said characterizing parameter; and (ii) automatically selecting one or more of the measured spectral data sets for which the classification applied to said one or more measured spectral set matches the prescribed set of one of more classification types; and
(c) using the selected one or more measured spectral data sets for each characterizing parameter to automaticalcalculate values for said characterizing parameters.

The statements and instructions for execution by the processor may be further configured to perform step (d) of transmitting to the remote client a listing of available characterizing parameter determinations for which the values were determined in step (c).

The statements and instructions for execution by the processor may be further configured to convey an option to the remote client for obtaining one or more of the values determined in step (c) subject to financial payment.

According to a fifth aspect of the invention there is provided a of determining values for characterizing parameters of a vinification liquid based on multiple samples from a common batch of said vinification liquid, the method comprising the steps of:

(a) obtaining measured spectral data sets for the plurality of samples along with classifications automatically applied to said measured spectral data sets based on classification codes read from machine readable codes on sample containers in which the samples were spectroscopically scanned;

(b) for each of the characterizing parameters to be determined for said common batch of said vinification liquid, (i) looking up a prescribed set of one or more classification types required to determine said characterizing parameter; and (ii) automatically selecting one or more of the measured spectral data sets for which the classification applied to said one or more measured spectral sets matches the prescribed set of one of more classification types; and (c) using the selected one or more measured spectral data sets for each characterizing parameter to calculate values for said characterizing parameters.

Step (a) may comprise receiving the spectral data sets and the classifications applied thereto from a remote client via a communications network.

The method may include step (d) of transmitting a listing of available characterizing parameter determinations for which the values were determined in step (c) to a client.

The method may include step (e) of conveying an option to the remote client for obtaining one or more of the values determined in step (c) subject to financial payment.

According to a sixth aspect of the invention there is provided a method of labelling sample containers to be used in spectroscopic analysis of vinification liquids, the method comprising the steps of: (a) identifying a number of characterizing parameters for which calculated values are to be made available; (b) determining a number of unique sample container configurations required to calculate values for all of the characterizing parameters identified in step (a) under spectroscopic analysis of samples respectively disposed in said sample containers of said unique sample container configurations; and (c) creating a number of unique sample container labels that match the unique sample container configurations in number and each have a machine readable code from which a respective unique classification number can be read by a scanning device.

Each one of the number of unique sample container configurations preferably differs from each other one of the number of unique sample container configurations in terms of a reagent content of said sample container.

The unique sample container configurations may include an empty sample container configuration that lacks any reagent therein.

The method may include distributing labelled sample containers to a client in an amount containing only a partial selection of the number of unique sample container configurations based on an identification of select parameters of interest by the client.

BRIEF DESCRIPTION OF THE DRAWINGS

In the accompanying drawings, which illustrate an exemplary embodiment of the present invention.

DETAILED DESCRIPTION

Figure 1:
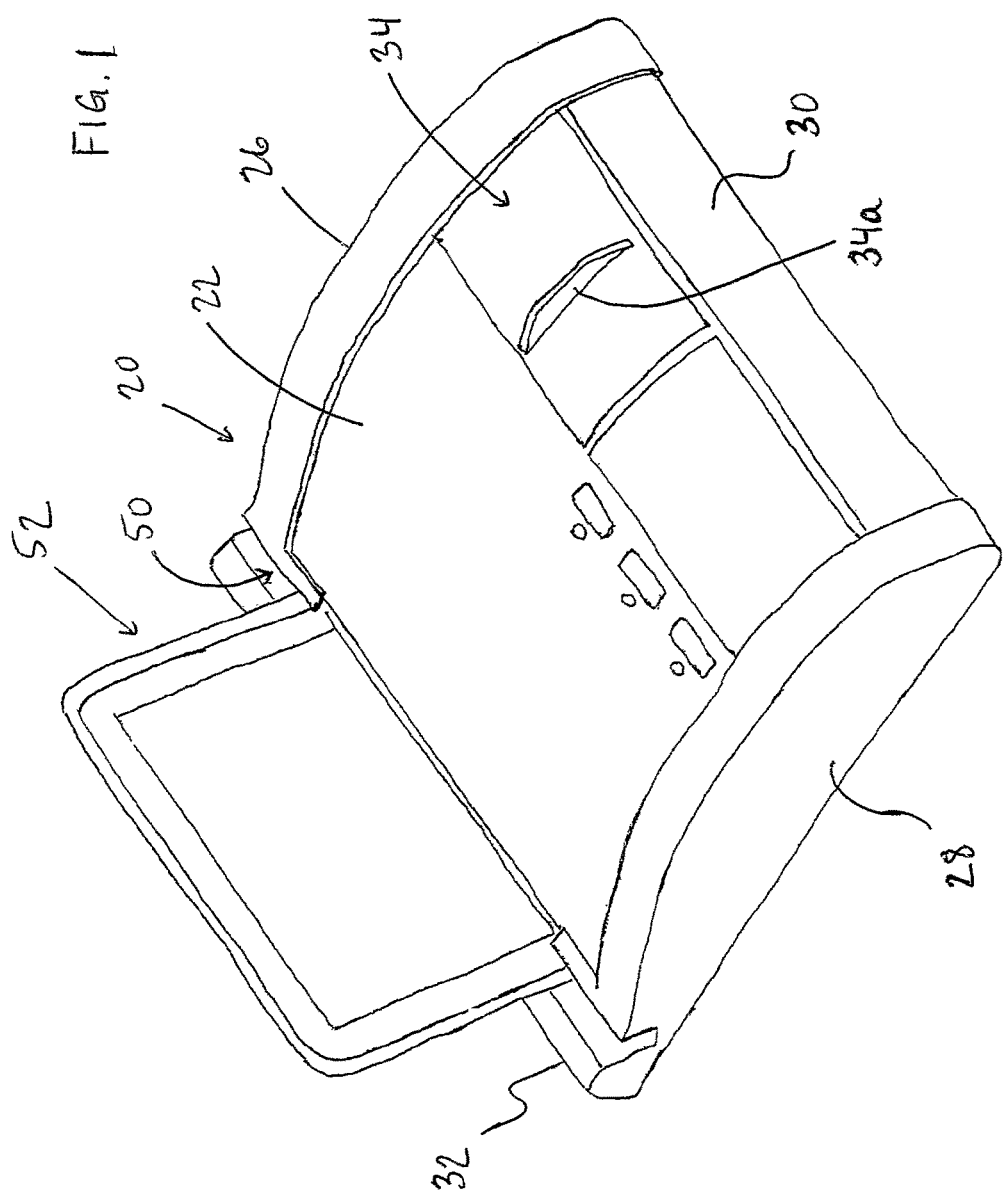
FIG. 1 is perspective view of a spectroscopic wine scanning apparatus of the present invention with an access door thereof in a closed position to conceal a sample holder of the apparatus.
Figure 2:
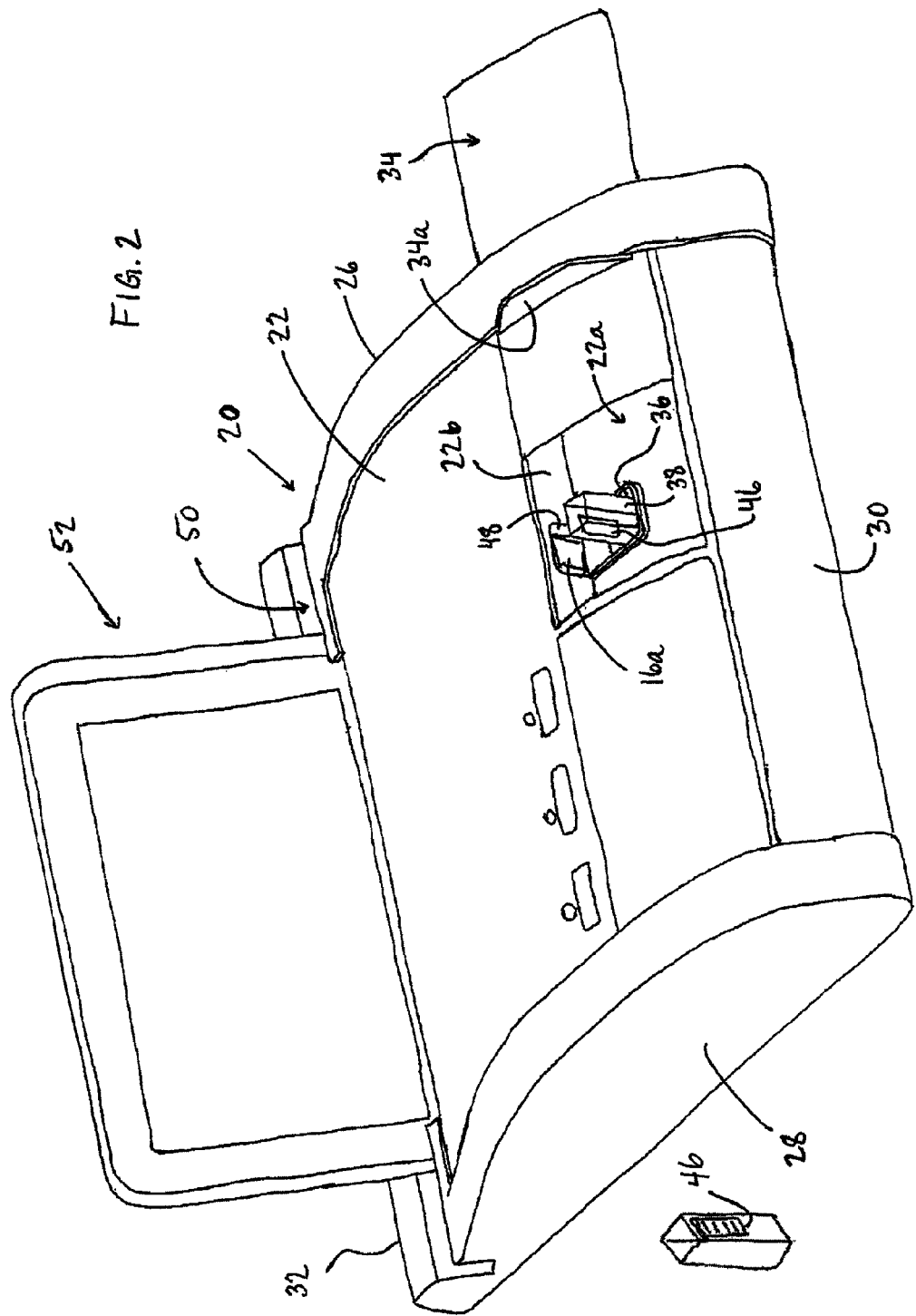
FIG. 2 is perspective view of the spectroscopic wine scanning apparatus of FIG. 1 with the access door thereof in an open position revealing access to the sample holder of the apparatus.
Figure 3:
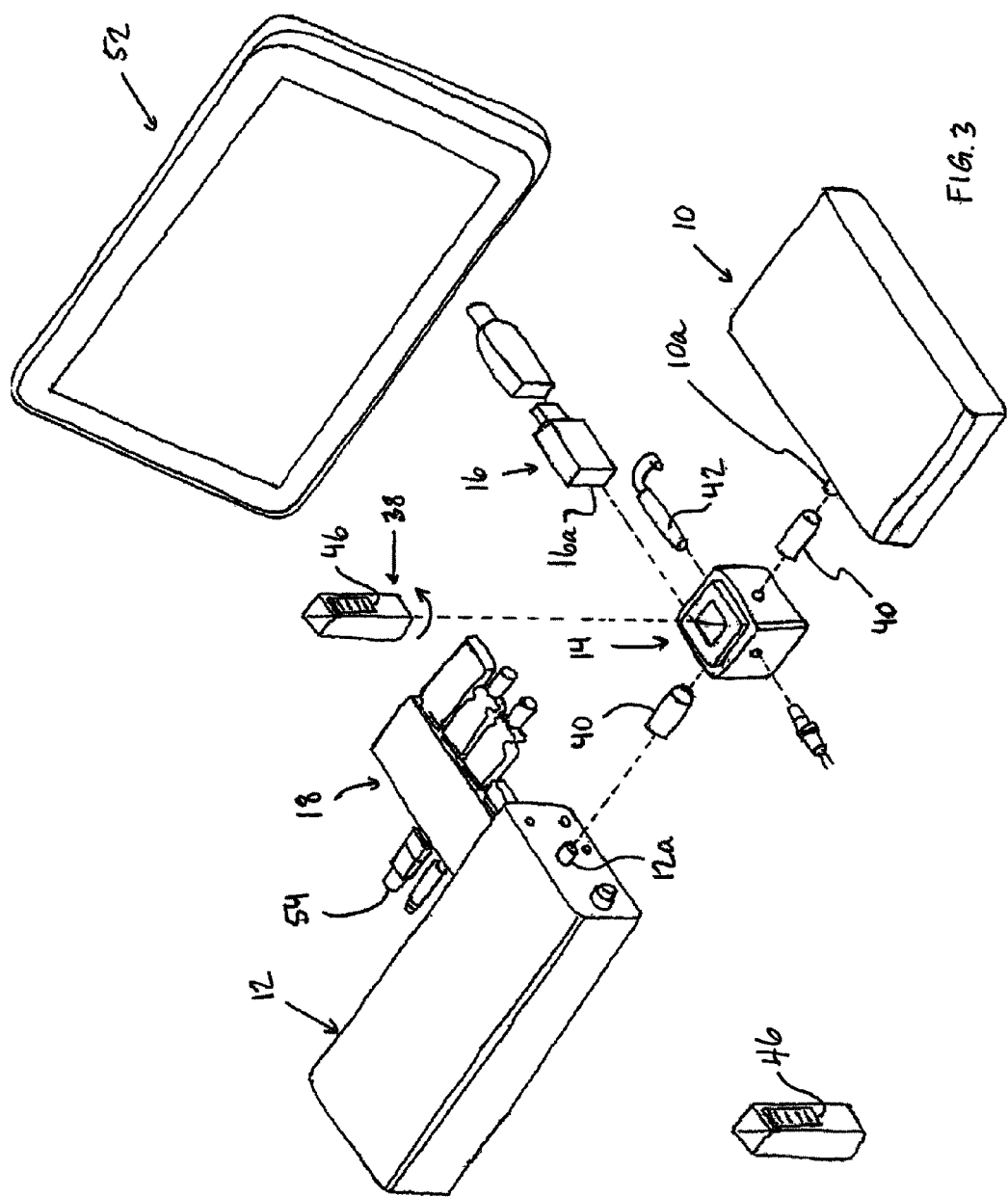
FIG. 3 is an exploded assembly view of components of the spectroscopic wine scanning apparatus of FIGS. 1 and 2 with a housing thereof removed to reveal internal components.

FIGS. 1 to 3 illustrate a spectroscopic wine scanning apparatus 1 of the present invention. With particular reference to FIG. 3, the apparatus 1 features a spectrometer 10, a light source 12, a cuvette holder 14 disposed between the spectrometer 10 and the light source 12, a barcode scanner 16, and a data hub 18. As shown in FIGS. 1 and 2, an external housing 20 contains all these components mounted within its interior. The housing 20 features a topside 22, an opposing bottom side 24 for placement atop a table or countertop or other suitable horizontal surface, two opposing side walls 26, 28 and opposing front and rear ends 30, 32. The spectrometer 10 resides adjacent the right side walls 26, and the light source 12 adjacent the left side wall 28, with the cuvette holder 14 disposed between them near the front end 30 of the housing.

The housing 20 features a movable access door or cover 34 that cooperates with a recessed area 22a of the housing's topside 22 that spans along the front end 30 of the housing from the corner between the right side wall 26 and front end 30 of the housing to near the midpoint of the front end 30. Via an upward projecting handle 34a on its upper face, the access door 34 is movable between a closed position (FIG. 1) fully covering this recessed area and an open position (FIG. 2) partially extended from over this space via a slot in the right side wall 26. An opening 36 in the recessed area 22a of the housing's topside 22 overlies the cuvette holder 14 in order to allow insertion and removal of a sample cuvette 38 to and from the cuvette holder via the opening 36 when the access door 34 is in the open position withdrawn from over the opening 36, which resides adjacent the end of the recessed area 22a near or at the center of the housing's width dimension, as measured between its two side walls 26, 28.

Referring again to FIG. 3, a light emission port 12a of the light source is coupled to a light inlet port on a respective side wall of the cuvette holder 14 that faces the light source, for example by a light transmission tube 40, and a light outlet port on the opposing side wall of the cuvette holder 14 is coupled to a light inlet port 10a of the spectrometer, for example by another light transmission tube 40. In a known manner, the tubes 40 and cuvette holder 14 thus define a light transmission path on which a beam of light emitted by the light source 12 travels through the cuvette 38 and the sample (liquid analyte or analyte/reagent mixture) contained within the cuvette, and continues onward into the spectrometer for measurement of the beam of light after passage thereof through the sample. The Light transmission tube may contain collimating lens to form parallel light beam inside the cuvette and optical filters to regulate the light intensity passing through the cuvette and incident onto inlet port 10a of the spectrometer.

The cuvette holder 14 is of a known type configured for seating of a rectangular curvette 38 between the opposing side walls of the holder at which the inlet and outlet light ports of the holder are defined. As shown, a temperature sensor 42 and light emitting diode (LED) or laser diode (LD) 44 may be provided at the two remaining walls of the rectangular cuvette holder 14 for known purposes. Particularly, a temperature sensor 42 provides a temperature measurement of the cuvette with sample in the holder 14, and an LED or LD 44 provide side illumination of sample in cuvette to initiate a detection of light scattering or fluorescence of sample with spectrometer 10. The barcode scanner 16 is positioned between the cuvette holder 14 and the rear end 32 of the housing within the interior thereof with the scanning end 16a of the scanner 16 facing toward the front end 30 of the housing 20 at a short height above the top end of the cuvette holder 14. With reference to FIG. 2, the scanning end 16a of the barcode scanner 16 is thus positioned to scan a barcode label 46 on the side of the rectangular cuvette 38 that faces the rear end 32 of the housing when seated in the cuvette holder 14. As shown, the barcode scanner may be positioned so as to scan the barcode label via a window opening 48 in a rear wall 22b of the recessed area 22a of the topside 22 of the housing 20.

By using a rectangular cuvette 38 and matching cuvette holder 14 whose cuvette-receiving opening is of similar rectangular shape, the barcode label 46 on the cuvette 38 is automatically aligned with the barcode scanner 16 so long as the cuvette is installed with the barcoded side facing the correct direction toward the rear of the housing. In the case of a linear or one-dimensional barcode, the barcode label extends along the axial direction of the cuvette, i.e. where the lines of the barcode thus lie in planes normal to the longitudinal axis of the cuvette, unlike the aforementioned prior art barcoded cuvettes in which the barcode labels lie circumferentially of a round cuvette and require that the cuvette be rotated about its longitudinal axis in order to read the barcode. The added complexity of a rotating cuvette holder is avoided, and the cuvette and holder remain stationary relative to all the other components in the housing during spectroscopic scanning of the sample in the cuvette.

The housing 20 is configured with a docking port 50 near the rear end 32 of the housing, for example in the form of a slot-shaped recess in the topside 22 of the housing 20 that runs fully across the housing from one side wall to the other a short distance ahead of the rear end 32 of the housing. A male Universal Serial Bus (USB) connector juts upwardly into this recess to engagement thereof with a female USB port found on a perimeter edge of a mobile tablet computing device 52. The relatively narrow width of the slot slightly exceeds the thickness of the tablet computer 52, whereby the slot-shaped port and rectangular housing of the tablet computer 52 cooperate under lowering the tablet into the docking port 50 into engagement with the USB connection in order to maintain an upright position of the tablet, whereby the tablet's display screen resides above the slot-shaped docking port 50 in a position facing forwardly over the topside 22 of the housing 20 toward the front 30 end thereof. The tablet computer 52 features a touchscreen display, whereby the user interacts with the graphical user interface of the operating system and various software applications of the tablet via physical fingertip interaction with the screen of the device.

The tablet computer 52 forms the control module of the apparatus 1, being used to trigger operation of the barcode scanner 16, and spectrometer 10, and to receive output data from the barcode scanner 16 and the spectrometer 10. The USB connector at the docking port 50 is on a USB cable 54, the other end of which is connected to the upstream port of the USB data hub 18. Three downstream ports of the data hub are occupied by connectors of cables that respectively link the hub to the spectrometer 10, barcode scanner 16 and temperature sensor 42. This way, the USB hub and the connections thereto defines a single communication link between the computer 52 and both the spectrometer and the barcode scanner 16. Accordingly, the attachable/detachable connection of the tablet computer 52 to the housing via the one USB connector establishes all the necessary communication links with the other components, avoiding the need to make multiple connections of the computer to the devices by way of multiple cables. The use of a general purpose tablet computer that is attachable and detachable to the housing allows the computer to be used for other purposes at either the same location of the housing, or any other location remote thereto. In addition, any wine analysis data stored on the memory of the computer can be easily taken to another location without having to send it by email or print it out, simply by detaching the mobile tablet computer from the housing and personally taking it to any intended destination.

Using the existing touch-screen of the tablet avoids the need for dedicated function controls on the housing. Other user-input devices may be connected to the tablet computer to interact with the user interface may be used instead of the touchscreen, while still avoiding the need for custom. For example, a mouse or trackball may be connected to the tablet computer (whether by cable or wireless connection) for such purposes, and may be connected via to the computer via a respective downstream port the USB hub of the apparatus. Spectrometers, light sources and barcode scanners connectable to a general purpose computing device via USB cables are well known and commercially available. Accordingly, the entire apparatus of FIGS. 1 to 3 can be produced with standard commercially available hardware components (tablet computer, spectrometer, light source, cuvette holder, barcode scanner, USB hub), and requires only fabrication of the housing and the addition of suitable control software to the tablet computer. Accordingly, the apparatus can be economically produced.

Having described the physical structure of the apparatus 1, its general operation is now described. In a conventional manner, the tablet computer 52 features a processor that is connected to computer readable memory on which software applications are stored for execution of statements and instructions in the software code by the processor. In addition to any of a variety of different software programs that the computer may be configured with, it includes software for operating a wine scanning procedure of the present invention.

The software presents a touchscreen graphical user interface (GUI) on the touchscreen display of the tablet computer, which may present a startup screen on which selectable options are presented, such as an option to review wine parameters that may have been obtained from previous spectroscopic wine analyses performed with the same apparatus 1, and an option to conduct a new wine analysis.

After selecting the latter option, the GUI preferably prompts the user to enter a name or other unique identifier for the batch or lot of wine that the user wishes to analyze, whereby the results of the parameter determination process of the analysis can later be easily matched up to the corresponding batch or lot by the user's recognition of the batch or lot identifier.

The user will have access to at least one set of cuvettes that serve as containers for the wine analyte that is to be tested. Each cuvette in a given set will have a different barcode label 46 affixed to a wall of the cuvette 38, as described above. Each of these barcode labels in the set of cuvettes differs from the others in that its barcode is unique from that of the other labels in the same set of cuvettes. Each cuvette in the set is unique from the other cuvettes in terms of its reagent content, and each unique barcode in the set matches up with a respective one these unique cuvettes. The difference in reagent content from one cuvette to the next may refer to the presence or lack of any reagent (i.e. an empty cuvette with no reagent may be part of the set), to a difference in the type of reagent material or combination of reagent materials present in the cuvettes, or to a difference in the amount or concentration of one or more reagents present in the cuvettes. The machine readable code data passed to the tablet computer by the barcode scanner based on the scanning of the barcode defines, or at least includes, a classification identifier that serves as an indication of the 'cuvette type', which the software compares against a predetermined listing of classification identifiers stored in the computer readable memory. Matching the machine-read classification identifier from the cuvette to a matching entry in the predetermined list confirms that the scanned barcode is compatible with the system of the present invention, i.e. the cuvette is recognized as being suitable for use by the apparatus 1.

The cuvette barcode labels and reagent contents are not added to the cuvettes by the user of the apparatus 1 (e.g. winery personnel), but rather are factory or laboratory prepared by a supplier, which may be the same entity as the manufacturer or distributer of the spectroscopic wine scanning apparatus 1, or a separate or related entity approved by the apparatus manufacturer. A set of cuvettes provided to the user by the supplier may correspond to the total number of unique barcodes that have been developed for the system, or alternatively a partial selection of the total number of cuvette types. For example, if the user wishes to obtain parameter values for each and every parameter that the system has been configured to determine, then the user orders a 'full set' of cuvettes (i.e. a set that is equal in number to the number of unique barcodes) from the supplier. However, if the user (e.g. winery) is only interested in determining a select limited number of parameters (either as standard practice for that winery, or in relation to the current wine batch or lot), they may choose to only order a lower-cost smaller set of cuvettes that is sufficient to determine the selected parameters, but insufficient to determine all possible parameters. The user would place the cuvette order based on their selected parameters of interest, rather than by the cuvette type.

For example, "Parameter A" of a wine may be determinable from a spectroscopic scan of a pure wine sample that has not been reacted with any reagent. This may correspond to a "Type A" cuvette, i.e. an empty cuvette from the supplier that has zero reagent content within it. This way, when the user operates the apparatus 1 to perform a spectroscopic scan of a "Type A" cuvette after adding the pure wine sample, the measured spectral data from this sample will be sufficient to determine a value for 'Parameter A' for the user's batch of wine.

"Parameter B" of a wine may require a spectroscopic scan of a sample that contains a mixture of the wine with "Reagent Chemical B" in order to determine a value for "Parameter B". Accordingly, a cuvette of "Type B" that is pre-filled with the required quantity of "Reagent Chemical B" by the supplier must be employed by the user in order to gain knowledge of "Parameter B". Accordingly, a user interested in "Parameter B" must obtain a "Type B" cuvette from the supplier, add the wine to the pre-filled "Reagent Chemical B" in the cuvette, and then perform the spectroscopic scan using the apparatus.

"Parameter C" may require a spectroscopic scan of a sample containing a mixture of the wine with "Reagent Chemical C" and "Reagent Chemical D" in order to determine a value for "Parameter C". Accordingly, a cuvette of "Type C" that is pre-filled with the required quantities of "Reagent Chemicals C and D" by the supplier must be employed by the user in order to gain knowledge of "Parameter C".

"Parameter D" may require an even more complex analysis, requiring both a scan of a first sample in a "Type A" cuvette (reagent free, pure-analyte sample) and a scan of a second sample in a "Type B" cuvette (mixed sample of analyte and Reagent Chemical B). Accordingly, a user interested in determining Parameter C must order a set of cuvettes including both cuvette Type A and cuvette Type B.

Other parameters may require more than two cuvette types to make a determination. Accordingly, the manufacturer or supplier will have a full listing of all testable parameters for which they have spectroscopic analyses techniques and the particular type(s) of cuvette needed to measure each such parameter. They may present users the ability to place an order from a list of available parameter determination options. Such an order may be based on individual parameters, or pre-defined parameter packages, from which the customers or clients (e.g. wineries) may select in order to obtain their optimal balance between cost, and the parameters in which they have particular interest.

The classification identifier in each machine-readable code detectable from the cuvette scanned by the barcode scanner thus identifies the cuvette type of the scanned barcode to the computer 52. The scanning process preferably starts by an on-screen 'barcode scan' option presented to the user after entering the batch/lot name. User selection of this option triggers the barcode scanner to perform a scan of the cuvette that has been placed in the holder, and communicate the scanned code to the computer. If no code was detected, or a scanned code doesn't match the prescribed code format expected by the software, an error message is conveyed to the user. For example, a barcode label may be applied to only one side of the rectangular cuvette in order to minimize labelling costs, in which case the user may inadvertently place the cuvette in the holder in an orientation in which the barcode label doesn't face the scanner 16. In the event of an error, the user should open the access door, and check that a system-compatible barcoded cuvette has been inserted, and is in the correct orientation and in the proper fully seated position of the holder. When a barcode is successfully scanned, and the classification identifier is matched to a listed identifier by the software in order to confirm that the cuvette is system compatible, the software may then automatically send 'start' signal to the spectrometer via the USB communication link in order to trigger a spectroscopic scan of the liquid sample in the cuvette, or may first prompt the user to provide a 'start' command via the touchscreen before taking such action.

In one embodiment, the light source is always 'on', meaning that it is initially powered up when connecting or turning on the tablet computer in preparation for a wine analysis procedure. In such cases, the computer need not be linked in any way to control the light source, and so the 'start' command from the user is used only to trigger operation of the spectrometer. However, other embodiments in which the light source is activated in response to an incoming signal from the computer are also possible within the scope of the present invention. The software on the tablet computer may be configured to setup or initialize the spectrometer upon when the software is initialized. For example, it is known that commercially available spectrometers capable of use for many different applications can be operated with many different sensitivities, modes etc., and accordingly require setup of such spectrometer parameters before measuring a spectrum. Accordingly, the software should perform such a setup when the software is initialized, or upon detecting that the spectrometer has been turned on after the software is already running. In the case of an off-the-shelf computer-controlled spectrometer, the setup may be achieved by cooperation with operational software provided by spectrometer supplier. In embodiments configured to maximize user-friendliness to non-specialized personnel, the software on the tablet computer is configured to setup the spectrometer to a pre-determined status as a part of switch-on or initializing procedure of the apparatus as a whole, and to maintain these same settings throughout any wine scanning procedures. However, in other embodiments, for more precise measurements, the spectrometer settings may be changed between wine sample scans, but reduces user-friendliness for non-specialized personnel, and may increase the risk of inaccurate or erroneous results depending on the particular user.

When the spectroscopic scan of the sample is complete, the measured spectral data from the spectrometer is sent to the computer 52 via the USB communication link, whereupon the computer 52 stores the measured spectral data from this scan in association with both the batch/lot identifier and the classification identifier that was read by the barcode scanner to serve as an indicator of the "cuvette type". This process of adding the wine to a barcoded cuvette, placing the cuvette in the cuvette holder, closing the access door of the housing over the seated cuvette scanning the barcode of the cuvette, spectroscopically scanning the cuvette and storing the measured spectral data is repeated as necessary using samples from the same batch or lot of wine until a full 'set' of cuvettes has been analyzed (i.e. enough uniquely barcoded cuvettes to determine the selected parameter(s) of interest). The access door of the housing should be closed once the cuvette is properly seated in the cuvette holder, either before or after the barcode scan, to avoid a wrong spectral measurement because of outside light penetration into the spectrometer.

Figure 4:
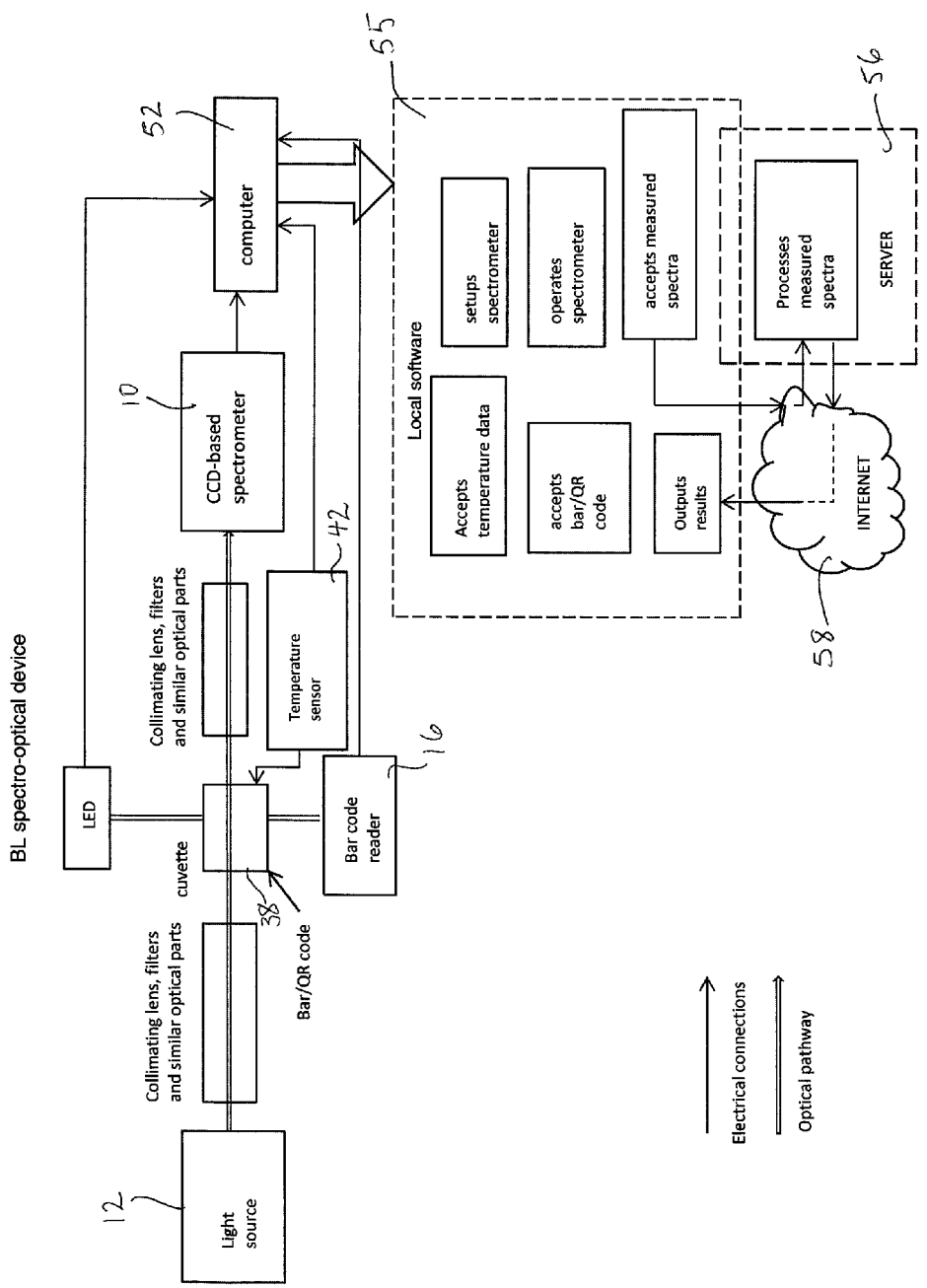
FIG. 4 is a schematic diagram of a spectroscopic wine analysis system employing the spectroscopic wine scanning apparatus of FIGS. 1 to 3.

Turning to FIG. 4, the illustrated embodiment of the invention employs a remote server 56 managed by the manufacturer, supplier or other system administrative entity for processing of the spectral data from the user's spectroscopically scanned set of cuvettes in order to generate useful values for sending back to the user on the parameter(s) of interest. The scanning apparatus thus acts as a remote terminal that electronically communicates with the server over a suitable network, whether via a wired or wireless connection of the tablet computer of the apparatus to the network. Handling of the data processing functions off-site at a location remote from the winery or other site of the scanning apparatus 1 has numerous potential advantages. The local software 55 on the tablet computer 52 of the scanning apparatus 1 is simplified by not requiring built-in complicated algorithms for processing the spectroscopic data to obtain meaningful parameter values, which reduces the processing load on the tablet computer, results in a reduced need for software updates if the administrative entity wishes to change the algorithms that process the spectral data, and keeps such potentially proprietary analysis algorithms in the exclusive possession of the administrative entity. However, other embodiments in which the post-scan processing of the spectral data is performed locally on the computing device 52 of the scanning apparatus 1 are also contemplated within the scope of the present invention.

The spectral data obtained by the tablet computer 52 of the apparatus for each cuvette is forwarded to the remote server 56 via a data network, such as the internet 58, together with the wine batch identifier and cuvette classification identifier corresponding to the scanned cuvette. This data may be automatically transferred after completion of each individual scan, or automatically transferred only once an entire set of cuvettes has been scanned. A client or user identifier also accompanies the spectral data, by which the server can track the particular user (e.g. winery) from whom the spectral data in question is received so that the final results of the data processing can be reported back to the correct user. As an alternative to automatic transfer of the data by the tablet software that controls the spectroscopic scanning procedure, the software may compile the data from a scanned set of cuvettes into a file stored locally on the tablet computer, which is then transferred to the server via an online interface visited by the user (e.g. a website hosted or administered by the administrative entity) via a separate program (e.g. a conventional web browser). Via a website login procedure, the server will recognize the user (based on a previous user registration process, for example completed when the scanning apparatus is purchased or delivered to the user), and accordingly will automatically tag the uploaded spectral data with an appropriate client identifier. The server features, or is connected to, a database in which the measured spectral data from each scanned cuvette is stored in association with the cuvette classification identifier, batch identifier and client identifier.

The computer readable memory of the server stores the software whose statements and instructions are executed by the server's processor in order to perform the algorithms for processing the spectral data to generate a value for one or more of the parameters of interest to the user/client. The algorithm first checks that for a given client identifier and batch identifier, spectral data has been received for a sufficient number of cuvette classifications to calculate one or more parameter values. If spectral data has been received for the required cuvette classifications for the parameter in question, the sets of spectral data tagged with these cuvette classifications for the batch/client combination in question is extracted from the database, and processed to calculate a value for the parameter. The server may be configured to calculate any and all parameters for which spectral data on the prescribed number of cuvette classifications has been received for that batch/client combination, or only calculate parameters which have been tagged as parameters of interest to the client. In one embodiment, where any/all possible parameter calculations are automatically conducted by the sever based on the scanned cuvette types or classes, the client may log into a website (which may be a same website via which the client selectively uploads spectral data if the data is not conveyed to the server via the scanning software 55) at which the client can view a listing of the different parameters for which results have been calculated and are available for review.

Release of the calculated parameter value to the client (for example for viewing on the website, and/or compilation into a report that is downloadable by or transmittable to the client, for example by e-mail) for one or more parameters may be made subject to payment by the client, which preferably can be performed by online electronic funds transfer via cooperation between the website and an online payment resource associated with the website. For example, in one embodiment, by purchasing a set of cuvettes according to one or more parameters of interest specified by the client when ordering the cuvettes, the client may be entitled to receipt of the calculated parameter results for each of the originally-purchased parameters of interest. However, the same combination of cuvette types used to determine the one or more originally-purchased parameters of interest may also be sufficient to calculate one or more other parameters.

Accordingly, by presenting a list of available parameter calculation results in the online interface, the client has the ability to purchase additional results that are available without having to go back and perform any further scans of the same batch or lot of wine. The server preferably continues to store the received spectral data even after the parameter determination process is completed, whether in the same database or a separate 'archived' resource, whereby the client is able to later obtain historical results through the online interface. This way, if a later batch of wine is found to be of poorer quality than a previous batch, then the client can purchase additional parameters from the current batch and prior historical batch in order to find the source of the discrepancy between the two batches if the already possessed parameter values for the two batches don't reveal such information.

While the forgoing embodiments are described for the use of analyzing wine, the analyte may be a vinification liquid other than the final wine product resulting from the overall vinification process, as spectroscopic analysis of such liquids are also known. The barcode may be a one-dimensional barcode, or a linear/one-dimensional barcode or a matrix/two-dimensional barcode, such as a Quick Response Code (commonly referred to as a QR code). Additional information beyond the classification code may be embodied within the barcode. For example, it is known that QR codes may be configured in a manner that triggers a web browser of a mobile computing device (e.g. tablet computer or smart phone) to visit a website for which the Uniform Resource Locator (URL) is coded within the QR code. Accordingly, QR codes on the cuvettes may be configured so that scanning of the QR code with a mobile device (for example, the tablet computer 52 of the scanning apparatus) will cause the device to run its web browser application and direct the web browser to the website of the administrative entity, where the user/client can login to gain access to various tools, including access to the parameter retrieval tool for any scanned and processed lots/batches, access to online ordering of cuvettes, access to online payment for cuvette orders or calculated parameter retrievals, and access to account updating tools (for change of cuvette delivery address, billing or payment information, etc.).

While the illustrated embodiment employs a detachable, mobile general computing device as the control module for the scanning apparatus 1, other embodiments may employ a stationary desktop or workstation computer to which the apparatus can be connected by USB or other communication interface, or employ a dedicated computerized control module built into the apparatus. While the illustrated embodiment uses USB connections between the components, other modes of wired or wireless communication may be employed between the components of the apparatus.

As examples of suitable off-the-shelf components that may be employed for the scanning apparatus, a BLUE-wave miniature spectrometer by StellarNet may be employed as a suitable CCD spectrometer with a USB interface for performing a full-spectrum spectral scan of each cuvette, and a compatible StellarNet light source may be employed as the cooperating light source. The BLUE-wave miniature spectrometer is powered by the tablet computer via the USB interface and thus requires no separate power supply. One or more onboard power supplies may be provided in the housing for coupling to mains power and providing power to the data hub and light source.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. System for spectroscopic analysis of vinification liquids to assess one or more characterizing parameters thereof, the system comprising:
   a plurality of different reagents;
   a sample container for holding a test sample comprised of vinification liquid and one or more of said different reagents, said sample container having thereon a respective machine readable code corresponding to a respective spectroscopic test utilizing said one or more of the reagents; and
   a scanning apparatus comprising:
   a sample holder arranged to support the sample container with the test sample held therein;
   a light source arranged relative to the selected sample holder to direct a beam of light into the test sample in the sample container when the selected sample container is supported by the sample holder;
   a spectrometer arranged relative to the sample holder to receive and measure the beam of light after interaction thereof with the test sample in order to perform a spectroscopic scan of the test sample and generate measured spectral data thereon;
   a scanning device positioned relative to the sample holder to scan a machine readable code on the sample container when the sample container is supported by the sample holder; and
   a computing device in communication with the spectrometer and the scanning device, the computing device being configured to apply the respective classification code from the scanned machine readable code to the measured spectral data of the test sample.

2. The system of claim 1 wherein the light source, the spectrometer and the scanning device are all contained within a common housing.

3. The system of claim 2 wherein the housing comprises an openable and closable access cover movable between a closed position concealing the sample holder and an open position revealing access to the sample holder.

4. The system of claim 2 or wherein the computing device is a mobile general computing device and the housing comprises a docking port having a communication connector to which the mobile general computing device is detachably connected to establish a communication link of the mobile general computing device with both the spectrometer and the scanning device.

5. The system of claim 4 wherein the docking port supports the mobile general computing device on the housing in a working position in which a display screen of the general computing device is visible at an exterior of the housing.

6. The system of claim 5 wherein the docking port is positioned proximate a rear end of the housing and configured to face the display screen forwardly over a topside of the housing toward an opposing front end of the housing, the sample holder being accessible from the topside of the housing at a location between the docking port and the front end of the housing.

7. The system of claim 4 wherein the mobile general computing device comprises a processor, a touchscreen display defining the display screen, and computer readable memory having stored thereon statements and instructions for execution by the processor to display a touchscreen graphical user interface of an application for controlling the spectrometer and managing the measured spectra data from said spectrometer.

8. The system of claim 1 wherein the computing device comprises a processor, a display, and computer readable memory having stored thereon statements and instructions for execution by the processor to (a) display a graphical user interface of a software application and (b) via said graphical user interface, perform the steps of (i) prompting a user to enter batch identification information for the vinificition liquid of the test sample; (ii) in response to confirmation of receipt of the sample container and the test sample held therein at the sample holder, reading the machine readable code from the sample container; (iii) subject to successful reading of the machine readable code, triggering the light source and the spectrometer to perform said spectroscopic scan; and (iv) receiving the measured spectral data from said spectroscopic scan and storing said spectral data in association with both the batch identification information and the classification applied to said spectral data.

9. The system of claim 8 wherein the statements and instructions for execution by the processor are further configured to transmit the measured spectral data to a remote server via a communications network for further processing of the spectral data to determine a quantitative measurement for one or more parameters of the batch of vinification fluid.

10. The system of claim 1 comprising a data hub electronically connected to the spectrometer and the scanning device to at least partly define a single communication link by which the spectrometer and the scanning device communicate with the computing device.

11. The system of claim 1 in which the sample holder and the scanning device are arranged to remain stationary relative to one another during scanning of the machine readable code.

12. The system of claim 1 further comprising computer readable memory connected or connectable to the computing device of the scanning apparatus, said computer readable memory storing therein a parameter listing comprising a plurality of different characterization parameters for vinification fluids, and for each parameter, identification of one or more spectroscopic tests that are necessary to calculate a parameter value for said parameter, wherein a processor connected to said computer readable memory is arranged to compare the respective classification code applied to the measured spectral data against the parameter listing to identify which of the different parameters are determinable from the measured spectral data.

13. The system of claim 12 wherein the computer readable medium and the processor are embodied by a server located remotely of the scanning apparatus.

14. The system of claim 1 in combination with a batch of vinification liquid for mixing with the different reagents to prepare the respective test samples for the plurality of sample containers.

15. Method for spectroscopic analysis of vinificition liquids, the method comprising the steps of:
(i) obtaining a batch of vinification fluid, a plurality of different reagents and a collection of sample containers having respective machine readable codes thereon that store respective classification codes corresponding to respective spectroscopic tests that respectively utilize the different reagents; and
(ii) for each sample container:
(a) adding a sample from the batch of vinification fluid to the respective reagent corresponding to said sample container to form a respective test sample;
(b) scanning the respective machine-readable code on said sample container;
(c) performing a spectroscopic scan of the respective test sample in said sample container to obtain a measured spectral data set on said respective test sample;
(d) automatically applying the classification code from the scanned machine readable code of said sample container to the measured spectral data set of the test sample of said sample container.

16. The method of claim 15 further comprising step (iii) of transmitting the measured spectral data set and applied classification for each test sample to a remote server at which values for different characterizing parameters of the batch of vinification liquid are calculated by selecting, for each characterizing parameter, one or more of the measured spectral data sets for which the applied classification code matches a prescribed spectroscopic test needed to calculate the characterizing parameter according to a parameter listing stored by the server; and using the selected one or more measured spectral data sets to have the server calculate the characterizing parameter.

17. The method of claim 15 further comprising step (iii) of calculating values for different characterizing parameters of the vinification liquid by (ii) selecting, for each characterizing parameter, one or more of the measured spectral data sets for which the applied classification code matches a prescribed spectroscopic test needed to calculate the characterizing parameter according to a parameter listing; and using the selected one or more measured spectral data sets to calculate the characterizing parameter.

18. System for spectroscopic analysis of vinificition liquids to assess one or more characterizing parameters thereof, the system comprising:
a sample holder arranged to support a sample container containing a sample of a vinification liquid;
a light source arranged relative to the sample holder to direct a beam of light into the sample in the sample container when the sample container is supported by the sample holder;
a spectrometer arranged relative to the sample holder to receive and measure the beam of light after interaction thereof with the sample in order to perform a spectroscopic scan of the sample and generate measured spectral data thereon;
a scanning device positioned relative to the sample holder to scan a machine readable code on the sample container when the sample container is supported by the sample holder; and
a computing device in communication with the spectrometer and the scanning device, the computing device being configured to apply a classification code from the scanned machine readable code to the measured spectral data of the test sample;
computer readable memory connected or connectable to the computing device, said computer readable memory storing therein a parameter listing comprising a plurality of different characterization parameters for vinification liquids, and for each parameter, identification of one or more of the spectroscopic tests that are necessary to calculate a parameter value for said parameter;

wherein a processor connected to the computer readable memory is arranged to compare the classification code applied to the measured spectral data against the parameter listing to identify which of the different parameters is determinable from the measured spectral data.

19. The system of claim 18 in combination with a batch of vinification liquid for providing the samples for the plurality of tests performed on the sample containers.

20. The system of claim 18 wherein the sample holder, the light source, the spectrometer, the scanning device and the computing device are components of a scanning apparatus, and the computer readable medium and the processor are embodied by a server located remotely of the scanning apparatus.

21. System for spectroscopic analysis of vinificition liquids to assess one or more characterizing parameters thereof, the system comprising:

a plurality of different reagents;

a sample container for holding a test sample comprised of vinification liquid and one or more of said different reagents, said sample container having thereon a respective machine readable code that stores a respective classification code corresponding to a respective spectroscopic test utilizing said one or more of said different reagents;

a sample holder arranged to support the sample container with the test sample held therein;

a light source arranged relative to the sample holder to direct a beam of light into the test sample in the sample container when the sample container is supported by the sample holder;

a spectrometer arranged relative to the sample holder to receive and measure the beam of light after interaction thereof with the test sample in order to perform a spectroscopic scan of the test sample and generate measured spectral data thereon;

a scanning device positioned relative to the sample holder to scan a machine readable code on the sample container when the sample container is supported by the sample holder; and a computing device in communication with the spectrometer and the scanning device, the computing device being configured to apply the respective classification code from the scanned machine readable code to the measured spectral data of the test sample;

computer readable memory connected or connectable to the computing device, said computer readable memory storing therein a parameter listing comprising a plurality of different characterization parameters for vinification liquids, and for each parameter, identification of one or more of the spectroscopic tests that are necessary to calculate a parameter value for said parameter; and wherein a processor connected to the computer readable memory is arranged to compare the classification code applied to the measured spectral data against the parameter listing to identify which of the different characterization parameters is determinable from the measured spectral data.

22. The system of claim 21 in combination with a batch of vinification liquid for mixing with the one or more of the different reagents to prepare the test sample.

23. The system of claim 21 wherein the sample holder, the light source, the spectrometer, the scanning device and the computing device are components of a scanning apparatus, and the computer readable medium and the processor are embodied by a server located remotely of the scanning apparatus.

* * * * *